United States Patent [19]
Moon et al.

[11] Patent Number: 5,851,834
[45] Date of Patent: Dec. 22, 1998

[54] METHODS FOR DETERMINING IMPURITY DISTRIBUTIONS IN MICROELECTRONIC STRUCTURES FORMED FROM ALUMINUM-CONTAINING MATERIALS

[75] Inventors: Sung-teak Moon; Sung-pil Choi; Dong-jun Lee, all of Kyungki-do, Rep. of Korea

[73] Assignee: Samsung Electronics Co., Ltd., Suwon, Rep. of Korea

[21] Appl. No.: 934,482

[22] Filed: Sep. 19, 1997

[30] Foreign Application Priority Data

Dec. 18, 1996 [KR] Rep. of Korea .................. 1996-67451

[51] Int. Cl.⁶ .................................................. G01N 13/00
[52] U.S. Cl. ........................ 436/5; 134/2; 134/3; 134/28; 134/41; 134/902; 436/80; 436/173; 436/175; 436/177; 438/115; 438/906
[58] Field of Search ............................... 134/2, 3, 28, 41, 134/902; 436/5, 80, 173, 175, 177; 438/115, 906, 101, 142

[56] References Cited

U.S. PATENT DOCUMENTS

| | | |
|---|---|---|
| 4,314,855 | 2/1982 | Cheng et al. .................. 134/3 |
| 4,890,151 | 12/1989 | Kemeda et al. .................. 357/65 |
| 5,214,283 | 5/1993 | Le .................................... 250/307 |
| 5,476,006 | 12/1995 | Fujii et al. ....................... 73/105 |
| 5,633,172 | 5/1997 | Shimezakio ..................... 436/5 |
| 5,688,755 | 11/1997 | Ikede et al. ..................... 510/254 |

*Primary Examiner*—Jeffrey Snay
*Assistant Examiner*—Sharidan Carrillo
*Attorney, Agent, or Firm*—Myers Bigel Sibley & Sajovec

[57] ABSTRACT

Impurity distributions in microelectronic structures formed from an aluminum-containing material are determined. A passivation layer, e.g., a titanium/titanium nitride layer or a borphosphosilicate glass (BPSG) layer, is formed on a substrate. A layer of the aluminum-containing material is formed on the passivation layer. The layer of the aluminum-containing material is then exposed to a phosphoric acid solution to remove aluminum from the layer of the aluminum-containing material and leave a precipitate on the passivation layer. The precipitate is then analyzed using scanning electron microscope (SEM) photomicrograms and/or Auger analysis to determine a distribution of impurities in the layer of the aluminum-containing material.

20 Claims, 6 Drawing Sheets

METHODS FOR DETERMINING IMPURITY DISTRIBUTIONS IN MICROELECTRONIC STRUCTURES FORMED FROM ALUMINUM-CONTAINING MATERIALS

FIELD OF THE INVENTION

The present invention relates to methods for testing materials, more particularly, to methods of testing materials in microelectronic structures.

BACKGROUND OF THE INVENTION

Microelectronic devices typically include a plurality of layers formed on a substrate, such as dielectric layers and conducting layers. The latter are commonly formed from metals. Metal layers may be formed by many techniques, such as vacuum evaporation, sputtering, and chemical vapor deposition (CVD).

Aluminum is commonly used for metal layers. Aluminum provides many advantages, including high electrical conductivity, the capability of forming good electrical connections with silicon and good adhesiveness to oxide layers such as silicon dioxide. Aluminum is also relatively easy to pattern using conventional photolithographic and etching techniques. Although aluminum offers these advantages, it can suffer from some disadvantageous phenomena such as electromigration. Electromigration refers to the migration of aluminum atoms caused by applied electric fields and heat generated by current passing though an aluminum conductor.

Pure aluminum generally has a high melting point, thus making it difficult to form good connections with structures such as silicon layers. Therefore, pure aluminum is generally not used to form layers in microelectronic devices. However, if impurities such as silicon or copper are introduced into aluminum, the resulting alloy exhibits a melting point which is lowered in comparison to pure aluminum. Accordingly, aluminum alloys containing small amounts of silicon, copper or other impurities commonly are used to form conductive layers in microelectronic devices.

However, poor distribution of impurities such as silicon and copper may cause problems. The impurities may become segregated from the aluminum, i.e., pockets of increased impurity concentration may be formed. Silicon impurities may also agglomerate into irregularly-shaped nodules. Segregation and nodule formation may cause etching processes to be incompletely performed or overdone, may lead to metal corrosion, and may increase electromigration and stress migration. In turn, leakage may be increased due to metallization failures or formation of spikes in an aluminum interconnection.

Aluminum alloys suitable for mass production of microelectronic devices have been developed and made commercially available, and are commonly used as target materials for vacuum evaporation or sputtering processes. The quantity of silicon, copper or other impurities in these commercially-available alloys typically is precisely controlled. However, the manner in which these impurities will be distributed in layers fabricated from these source alloys depends on factors which typically are outside of the control of the supplier of the alloy. For example, the manner in which the source alloy is handled or stored, or the processes employed to form a layer from the source alloy, may effect the distribution of impurities in the layer. Accordingly, it is desirable to provide techniques for evaluating impurity distributions in fabricated aluminum microstructures in order to improve device quality and yield.

SUMMARY OF THE INVENTION

In light of the foregoing, it is an object of the present invention to provide improved methods for determining impurity distribution in microelectronic structures formed from an aluminum-containing material.

This and other objects, features and advantages are provided according to the present invention by methods in which aluminum present in an aluminum-containing layer formed on a passivation layer is dissolved in a phosphoric acid solution, leaving behind a precipitate which is then analyzed to determine the distribution of impurities in the aluminum-containing layer. Preferably, the phosphoric acid solution includes a volume percentage of phosphoric acid in a range from 25 percent to 90 percent, and a volume percentage of deionized water in a range from 10 percent to 75 percent. The concentration of phosphoric acid preferably is proportional to the concentration of silicon in the aluminum-containing material from which the layer was formed. By forming the aluminum-containing layer on a passivation layer, unwanted factors may be reduced in the analysis. By using a passivation layer having a color which is distinctively different from the aluminum-containing layer, e.g., a titanium, titanium nitride or borophosphosilicate glass (BPSG) layer, a convenient indication of when the aluminum in the aluminum-containing layer is dissolved may be provided.

In particular, according to the present invention, impurity distributions in microelectronic structures formed from an aluminum-containing material are determined. A passivation layer, e.g., a titanium/titanium nitride layer or a borphosphosilicate glass (BPSG) layer, is formed on a substrate. A layer of the aluminum-containing material is formed on the passivation layer. The layer of the aluminum-containing material is then exposed to a phosphoric acid solution to remove aluminum from the layer of the aluminum-containing material and leave a precipitate on the passivation layer. The precipitate is then analyzed to determine a distribution of impurities in the layer of the aluminum-containing material.

According to a first aspect of the present invention, the layer of the aluminum-containing material is exposed to the phosphoric acid solution until a surface of the substrate changes color. The passivation layer may produce a first color on the surface of the substrate, and the layer of the aluminum-containing material may produce a second color on the surface of the substrate. The layer of the aluminum-containing material may be exposed to the phosphoric acid solution until the surface of the substrate changes from the second color to the first color. For example, the passivation layer may include at least one of titanium and titanium nitride, and the layer of the aluminum-containing material may be exposed to the phosphoric acid solution until the substrate changes to an green color.

The phosphoric acid solution preferably comprises a solution of phosphoric acid and deionized water, more preferably, a solution including a volume percentage of phosphoric acid in a range from 25 percent to 90 percent and a volume percentage of deionized water in a range from 10 percent to 75 percent. If the aluminum-containing material has a silicon content, the phosphoric acid concentration preferably is proportional to the silicon content of the aluminum-containing material.

The precipitate formed may be analyzed by producing an electron microscope image of a surface of the substrate and visually inspecting the image to determine a distribution of impurities in the layer of the aluminum-containing material.

The precipitate may also be analyzed by performing Auger Electron Spectroscopy (AES) of the substrate to determine a distribution of impurities in the layer of the aluminum-containing material. Preferably, the substrate is cleaned and dried before analysis.

BRIEF DESCRIPTION OF THE DRAWINGS

Some of the objects and advantages of the present invention having been stated, others will be more fully understood from the detailed description that follows and by reference to the accompanying drawings in which.

DETAILED DESCRIPTION OF PREFERRED EMBODIMENTS

Figure 1:
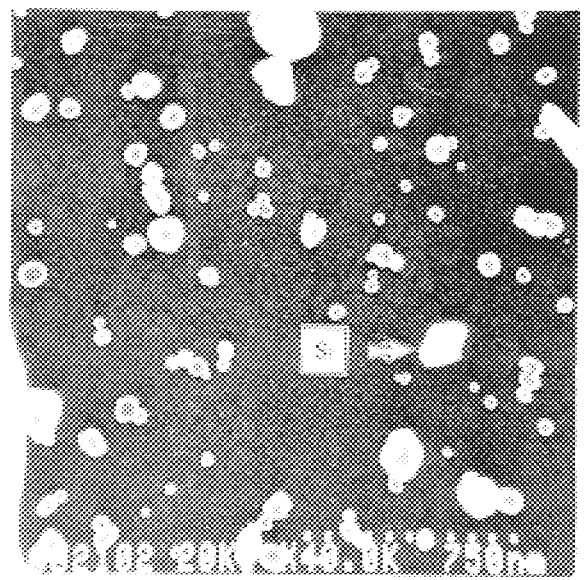
FIGS. 1–8 are scanning electron microscope (SEM) photomicrograms illustrating impurity precipitates formed on a substrate according to the present invention.

The present invention now will be described more fully hereinafter with reference to the accompanying drawings, in which embodiments of the invention are shown. Those skilled in the art will appreciate that the invention may be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements throughout.

According to the present invention, an aluminum-containing layer is formed on a substrate and a solution of phosphoric acid ($H_3PO_4$) and deionized water is used to selectively dissolve aluminum in the layer, allowing the distribution of impurities such as silicon and copper in the layer to be determined. The phosphoric acid solution preferably comprises a volume percentage of phosphoric acid in a range from 25 percent to 90 percent and a volume percentage of deionized water in a range from 10 percent to 75 percent. The concentration of phosphoric acid in the solution preferably is proportional to the amount of silicon in the aluminum alloy, that is, the less silicon present in the alloy, the lower the concentration of phosphoric acid in the solution should be.

Commonly-used aluminum alloys typically contain a weight percentage of silicon in a range from 0.1 percent to 2 percent. For example, one widely-used alloy includes 1 percent silicon, 0.5 percent copper and 98.5 percent aluminum (by weight), while another commonly used alloy includes 0.2 percent silicon, 0.5 percent copper and 99.3 percent aluminum (by weight). According to an aspect of the present invention, when treating an aluminum alloy layer formed from a quantity of aluminum alloy having less than 1.0 percent silicon by weight, a phosphoric acid solution including less than 30 percent phosphoric acid by volume is preferably used. If a higher concentration of phosphoric acid is used, silicon in the aluminum alloy layer may be dissolved, reducing the accuracy of the analysis.

Figure 11:
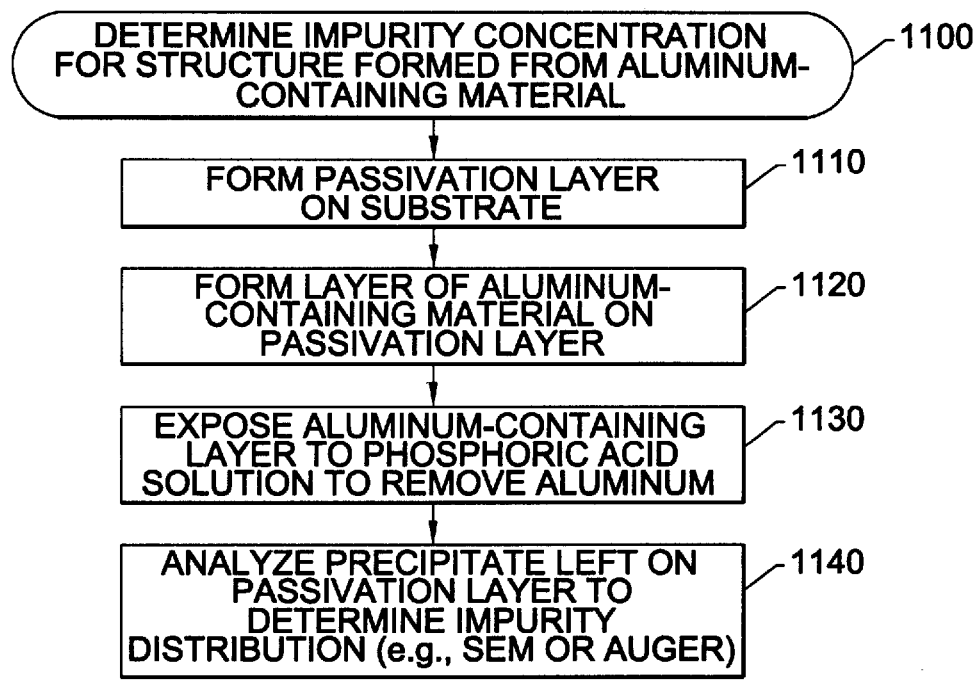
FIG. 11 illustrates operations for determining an aluminum-containing layer according to the present invention.

FIG. 11 illustrates operations (Block 1100) for determining a layer of aluminum-containing material according to the present invention. A passivation layer, e.g., a titanium, titanium nitride, or borophosphosilicate glass (BPSG) layer, is formed on a substrate (Block 1110). A layer of the aluminum-containing material is then formed on the passivation layer (Block 1120). The layer of the aluminum-containing material is then exposed to a phosphoric acid solution, e.g., immersed in the phosphoric acid solution, to remove aluminum from the layer of the aluminum-containing material and leave a precipitate, for example, a silicon or copper precipitate, on the passivation layer (Block 1130). The precipitate is then analyzed to determine a distribution of impurities in the layer of the aluminum-containing material (Block 1140).

The passivation layer provides protection for underlying structures on the substrate during formation and treatment of the aluminum layer, and can help reduce the influence of other factors that might affect analysis. The passivation layer also can provide a convenient way to determine when the aluminum in the aluminum-containing layer has been dissolved. Preferably, a titanium or titanium nitride layer is used, as these materials are particularly resistant to the phosphoric acid and produce a distinctive dark green color as the aluminum in the aluminum-containing layer is dissolved. Borophosphosilicate glass (BPSG) may also be used, which produces a distinctive dark orange color in contrast to the white or gray color of the untreated aluminum-containing layer.

The dissolution process may be accelerated if the phosphoric acid solution is heated to a temperature in a range from 50° C. to 80° C. Preferably, the solution is heated to a temperature in a range from 50° C. to 80° C., more preferably, to a temperature in a range from 64° C. to 66° C. The temperature of the phosphoric acid solution can be controlled by techniques well known to those skilled in the art.

After exposing the substrate to the phosphoric acid to remove the aluminum in the aluminum-containing layer, the substrate preferably is cleaned, and more preferably, cleaned by exposing the substrate to running deionized water. According to preferred embodiments, the deionized water is supplied at a rate in a range from 0.1 to 5 liters per minute, and more preferably, at a rate in a range from 2 to 4 liters per minute. Preferably, the substrate is cleaned for a time ranging from 30 seconds to 10 minutes, and more preferably, for a time ranging from 2 minutes to 5 minutes. The cleaned substrate then preferably is dried to remove moisture before analysis. This may be accomplished by blowing dry air over the substrate or by heating the substrate in an oven.

Analysis of the precipitate remaining on the substrate may be conducted using images of the substrate surface produced by a scanning electron microscope (SEM). The images may be visually inspected to determine the distribution of precipitates remaining on the passivation layer after the aluminum in the aluminum-containing layer is removed. Auger analysis, also known as Auger Electron Spectroscopy (AES), may also be performed. Auger analysis, well-known to those skilled in the art, takes advantages of unique electron emission characteristics of elemental components present on the surface of a sample to identify distribution of these components.

The inventors have experimentally evaluated aluminum sample alloy layers formed on titanium/titanium nitride and BPSG passivation layers formed on substrates. Each substrate included an aluminum alloy layer formed from one of three different alloys using techniques according to the present invention. A first one of the alloys (Alloy 1) included 1.0% silicon, 0.5% copper and 98.5% aluminum. A second one of the alloys (Alloy 2) included 0.2% silicon, 0.5% copper and 99.3% aluminum. The third alloy (Alloy 3) included 1.0% silicon and 99.0% aluminum.

The sample alloy layers were exposed to phosphoric acid solutions having two different concentrations of phosphoric acid. A first solution (Solution 1) included 150 ml of 85% phosphoric acid to 20 ml of deionized water. A second solution (Solution 2) included 50 ml of 85% phosphoric acid to 150 ml of deionized water. Each sample alloy layer was exposed to one of these solutions at a temperature of 65°±1° C. The treated substrates were then cleaned and dried as described above, and a scanning electron microscope was used to obtain detailed images of the surface of the substrate.

FIG. 1 is a SEM photomicrograph that shows a 40,000X image of a substrate upon which an aluminum alloy layer was formed using Alloy 1 and which was treated using Solution 1. A silicon precipitate Si is indicated on the photomicrograph.

Figure 2:
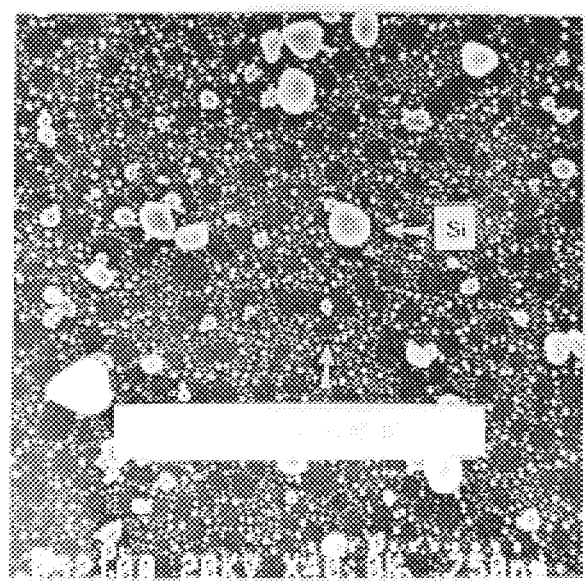

FIG. 2 is a SEM photomicrograph which shows a 40,000X image of a substrate upon which an aluminum alloy layer was formed on a Ti/TiN layer using Alloy 1 which was treated using Solution 2. A silicon precipitate Si is indicated on the photomicrograph.

Figure 3:
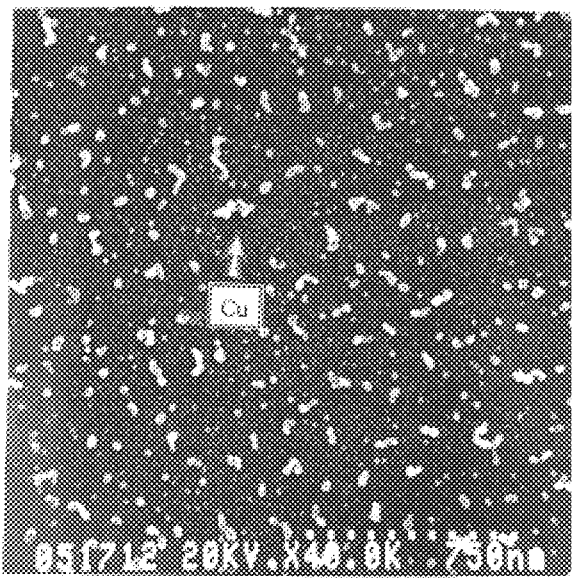

FIG. 3 is a SEM photomicrograph that shows a 40,000X image of a substrate upon which an aluminum alloy layer was formed using Alloy 2 and which was treated using Solution 1. A copper precipitate Cu is indicated on the photomicrograph.

Figure 4:
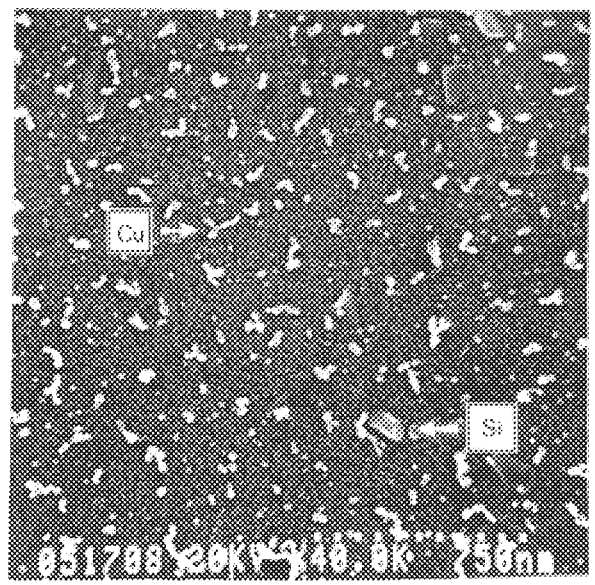

FIG. 4 is a SEM photomicrograph that shows a 40,000X image of a substrate upon which an aluminum alloy layer was formed using Alloy 2 and which was treated using Solution 2. A silicon precipitate Si and a copper precipitate Cu are indicated on the photomicrograph.

Figure 5:
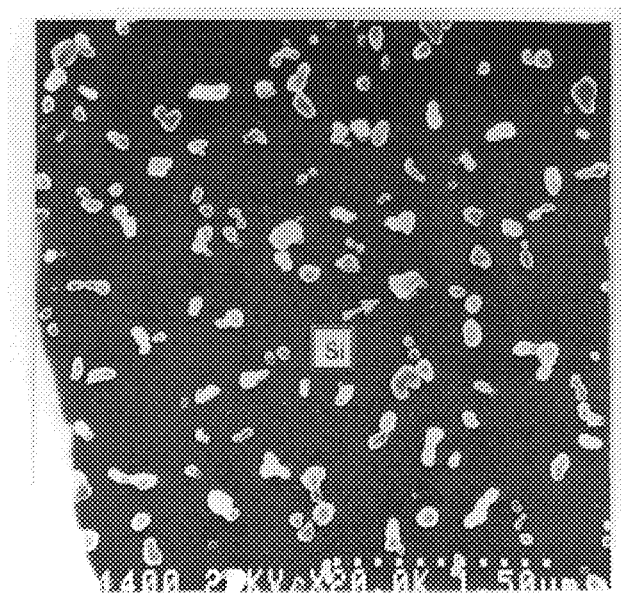

FIG. 5 is a SEM photomicrograph that shows a 20,000X image of a substrate upon which an aluminum alloy layer was formed using Alloy 3 and which was treated using Solution 1. A silicon precipitate Si is indicated on the photomicrograph.

Figure 6:
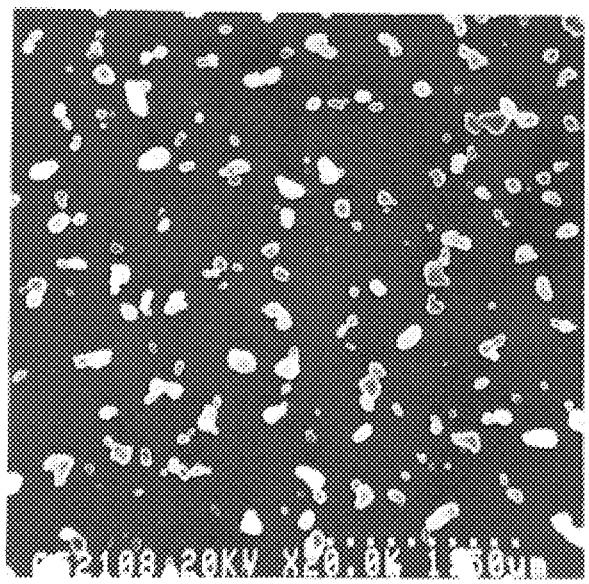

FIG. 6 is a SEM photomicrograph that shows a 20,000X image of a substrate upon which an aluminum alloy layer was formed using Alloy 3 and which was treated using Solution 2.

Figure 7:
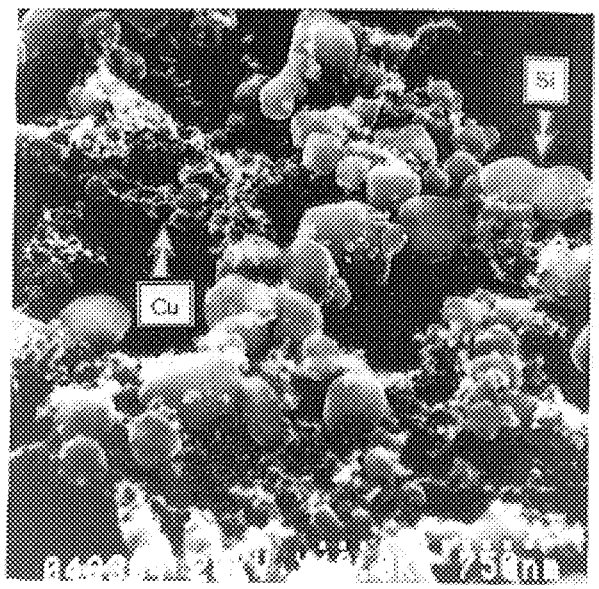

FIG. 7 is a SEM photomicrograph which shows impurity precipitates on a BPSG passivation layer. A silicon precipitate Si and a copper precipitate Cu are indicated on the photomicrograph.

Figure 8:
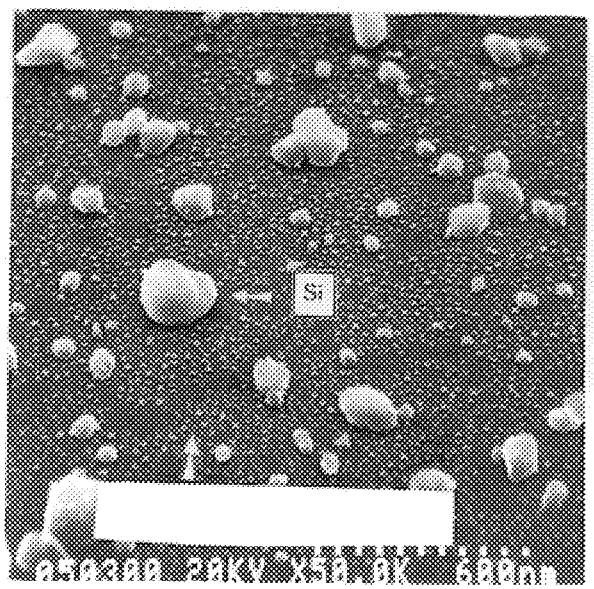

FIG. 8 is a SEM photomicrograph which shows impurity precipitates on a Ti/TiN passivation layer. A silicon precipitate Si is indicated on the photomicrograph.

Figure 9:
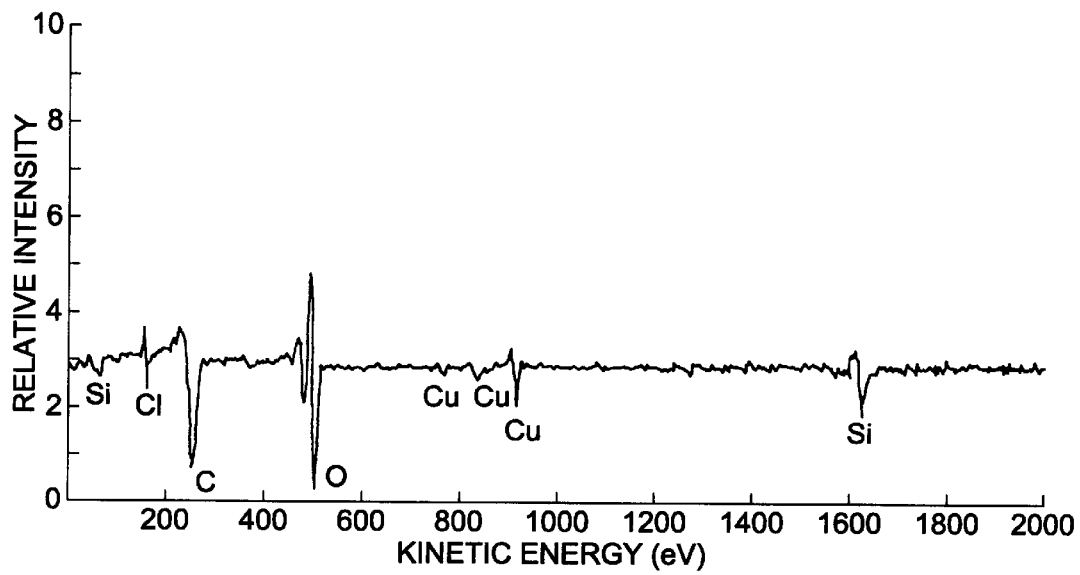
FIGS. 9–10 are Auger Electron Spectroscopy (AES) plots illustrating impurity distributions for precipitates formed on a substrate according to the present invention.
Figure 10:
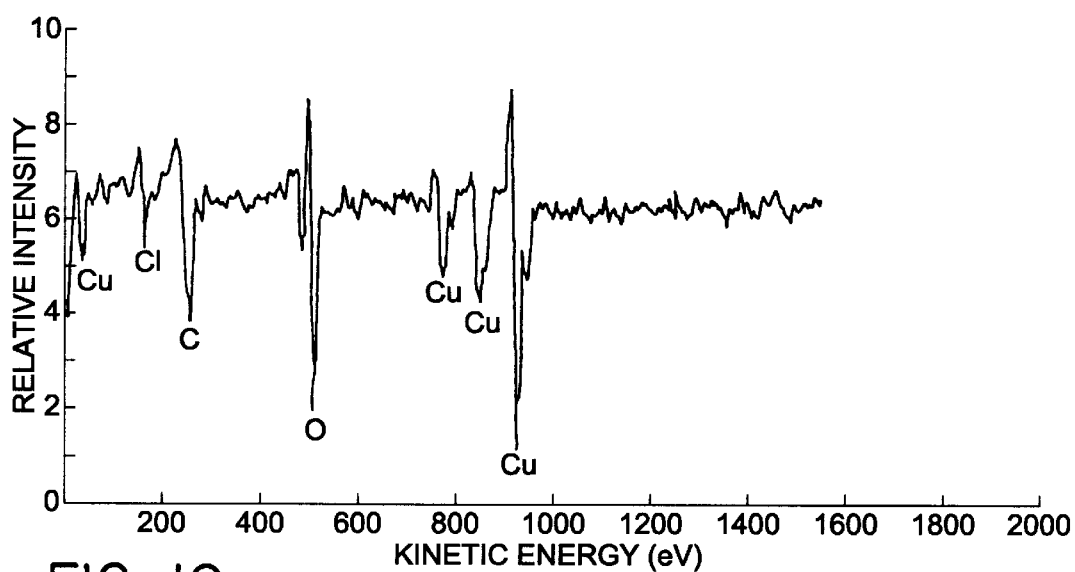

FIGS. 9 and 10 provide Auger analysis scan plots that indicate concentrations of impurity precipitates. As can be seen from these plots, silicon Si and copper Cu impurities are present.

A summary of analysis results for the sample alloy layers is provided in Tables I and II:

TABLE I

| | Distribution of Copper Impurities ($\mu$m) | | |
|---|---|---|---|
| | Solution 1 | Solution 2 | Remarks |
| Alloy 1 | 0.02–0.7 | 0.02–0.07 | distributed among Al grains |
| Alloy 2 | 0.02–0.07 | 0.02–0.07 | distributed widely |
| Alloy 3 | N/A | N/A | N/A |

TABLE II

| | Distribution of Silicon Impurities ($\mu$m) | | |
|---|---|---|---|
| | Solution 1 | Solution 2 | Remarks |
| Alloy 1 | 0.2–0.3 | 0.2–0.3 | not affected by concentration of phosphoric acid |
| Alloy 2 | none seen | 0.15–0.25 | affected by concentration of phosphoric acid |
| Alloy 3 | 0.2–0.3 | 0.2–0.3 | not affected by phosphoric acid concentration |

As can be seen from Table II, the accuracy of analysis can be affected by the phosphoric acid concentration for alloy layers formed from alloys with smaller amounts of silicon.

According to the present invention, methods of determining impurity distribution in aluminum-containing layers are provided which can be integrated into production processes. The methods can be used to analyze impurity distributions in situ, thus allowing production processes to be improved and increase device quality and yield.

For example, sample wafers may be placed in a manufacturing process that includes an alloy layer formation process. A sample alloy layer may be formed on the sample wafer and tested according to the present invention to provide information on the quality of the alloy layer formation process. This information may in turn be used to adjust process parameters, correct process defects and the like, thus allowing improvement in quality and yield for devices formed by the process.

In the drawings and specification, there have been disclosed typical embodiments of the invention and, although specific terms are employed, they are used in a generic and descriptive sense only and not for purposes of limitation, the scope of the invention being set forth in the following claims.

That which is claimed is:

1. A method of determining impurity distributions in microelectronic structures formed from an aluminum-containing material, the method comprising the steps of:

forming a passivation layer on a substrate;

forming a layer of the aluminum-containing material having impurities therein on the passivation layer;

exposing the layer of the aluminum-containing material to a phosphoric acid solution to remove an aluminum from the layer of the aluminum-containing material and leave said impurities on said passivation layer;

removing the phosphoric acid solution from said passivation layer to leave a precipitate of said impurities on said passivation layer; and analyzing the precipitate to determine a distribution of impurities in the layer of the aluminum-containing material.

2. A method according to claim 1, wherein said step of exposing comprises the step of exposing the layer of the aluminum-containing material to the phosphoric acid solution until a surface of the substrate changes color.

3. A method according to claim 2, wherein the passivation layer produces a first color on the surface of the substrate, wherein the layer of the aluminum-containing material produces a second color on the surface of the substrate, and wherein said step of exposing comprises the step of exposing the layer of the aluminum-containing material to a phosphoric acid solution until the surface of the substrate changes from the second color to the first color.

4. A method according to claim 3:

wherein said step of forming a passivation layer comprises the step of forming a passivation layer comprising at least one of titanium and titanium nitride; and wherein said step of exposing the layer of the aluminum-containing material comprises the step of exposing the layer of the aluminum-containing material to a phosphoric acid solution until the substrate changes from said second color to said first color, wherein said first color is a green color.

5. A method according to claim 3:

wherein said passivation layer comprises borophosphosilicate glass (BPSG); and wherein said step of exposing the layer of the aluminum-containing material comprises the step of exposing the layer of the aluminum-containing material to a phosphoric acid solution until the substrate changes from said second color to said first color, wherein said first color is an orange color.

6. A method according to claim 1, wherein the phosphoric acid solution comprises phosphoric acid and deionized water.

7. A method according to claim 6, wherein the phosphoric acid solution comprises a volume percentage of phosphoric acid in a range from 25 percent to 90 percent and a volume percentage of deionized water in a range from 10 percent to 75 percent.

8. A method according to claim 7, wherein the aluminum-containing material has a silicon content, and wherein said step of exposing comprises the step of exposing the layer of the aluminum-containing material to a phosphoric acid solution comprising phosphoric acid in a concentration proportional to the silicon content of the aluminum-containing material.

9. A method according to claim 1, wherein said step of analyzing comprises the steps of:

producing an electron microscope image of a surface of the substrate; and visually inspecting the image to determine a distribution of impurities in the layer of the aluminum-containing material.

10. A method according to claim 1, wherein said step of analyzing comprises the step of performing Auger Electron Spectroscopy (AES) of the substrate to determine a distribution of impurities in the layer of the aluminum-containing material.

11. A method according to claim 1, wherein said step of removing the phosphoric acid solution comprises the steps of:

cleaning the substrate; and drying the substrate.

12. A method according to claim 11, wherein said step of cleaning comprises the step of cleaning the substrate with deionized water.

13. A method according to claim 12, wherein said step of cleaning comprises the step of rinsing the substrate with deionized water at a flow rate in a range from 0.1 liters per minute to 5 liters per minute.

14. A method according to claim 12, wherein said step of cleaning comprises the step of exposing the substrate to deionized water for a predetermined time in a range from 30 seconds to 10 minutes.

15. A method according to claim 14, wherein said step of cleaning comprises the step of exposing the substrate to deionized water for a predetermined time in a range from 2 minutes to 5 minutes.

16. A method according to claim 1, wherein said step of forming a layer of the aluminum-containing material comprises the step of vacuum evaporating the aluminum material onto to the passivation layer.

17. A method according to claim 1, wherein said step of forming a layer of the aluminum-containing material comprises the step of sputtering the aluminum material onto to passivation layer.

18. A method according to claim 1, wherein said step of exposing comprises the step of exposing the layer of the aluminum-containing material to a phosphoric acid solution at a temperature in a range from 50° C. to 80° C.

19. A method according to claim 18, wherein said step of exposing comprises the step of exposing the layer of the aluminum-containing material to a phosphoric acid solution at a temperature in a range from 60° C. to 70° C.

20. A method according to claim 19, wherein said step of exposing comprises the step of exposing the layer of the aluminum-containing material to a phosphoric acid solution at a temperature in a range from 64° C. to 66° C.

* * * * *